United States Patent [19]

Villari et al.

[11] 4,372,313
[45] Feb. 8, 1983

[54] BODY DRAINAGE RECEPTACLE WITH ANTI-SEPTIC CATHETER CONTACT SURFACE IN RECEIVING POCKET

[75] Inventors: Frank K. Villari, Oak Park; James P. Cianci, Cary, both of Ill.

[73] Assignee: The Kendall Company, Boston, Mass.

[21] Appl. No.: 293,544

[22] Filed: Aug. 17, 1981

Related U.S. Application Data

[62] Division of Ser. No. 139,301, Apr. 11, 1980, Pat. No. 4,333,480.

[51] Int. Cl.³ .............................................. A61F 5/44
[52] U.S. Cl. .................................. 128/295; 128/767; 128/275; 128/DIG. 24
[58] Field of Search .............. 128/760, 767, 768, 771, 128/275, 295, DIG. 24, 260, 272; 4/144.1, 144.2, 144.3, 144.4

[56] References Cited

U.S. PATENT DOCUMENTS

| | | | |
|---|---|---|---|
| Re. 26,964 | 10/1970 | Coanda | 128/771 X |
| Re. 30,607 | 5/1981 | Manschot et al. | 128/768 |
| 3,212,221 | 4/1967 | Overment | 128/DIG. 24 |
| 3,626,980 | 12/1971 | Svensson | 128/295 |
| 3,908,656 | 9/1975 | Binard | 128/295 |
| 3,976,311 | 8/1976 | Spendlove | 128/295 |
| 4,000,649 | 1/1977 | Hanifi | 128/771 |
| 4,160,383 | 7/1979 | Rauschenberger | 128/295 |
| 4,232,677 | 11/1980 | Leibinsohn | 128/295 X |
| 4,233,263 | 11/1980 | Schaeffer | 128/DIG. 24 |
| 4,236,517 | 12/1980 | Langston et al. | 128/275 |

*Primary Examiner*—Richard J. Apley
*Assistant Examiner*—J. L. Kruter
*Attorney, Agent, or Firm*—Powell L. Sprunger

[57] ABSTRACT

A urine receptacle comprising, a container having a chamber for collection of urine, and a pocket on an outer surface of the container, with the pocket having an open end. The receptacle has a tubular section having an inner end attached to a lower portion of the container and communicating with said chamber, and an outer end. The receptacle has an elongated projection extending from the container in the pocket and being removably receivable in a lumen of the tubular section in the outer end in a storage position of the tubular section in the pocket. The projection has a device for contacting an inner surface of the tubular section and for retaining an antimicrobial agent.

7 Claims, 7 Drawing Figures

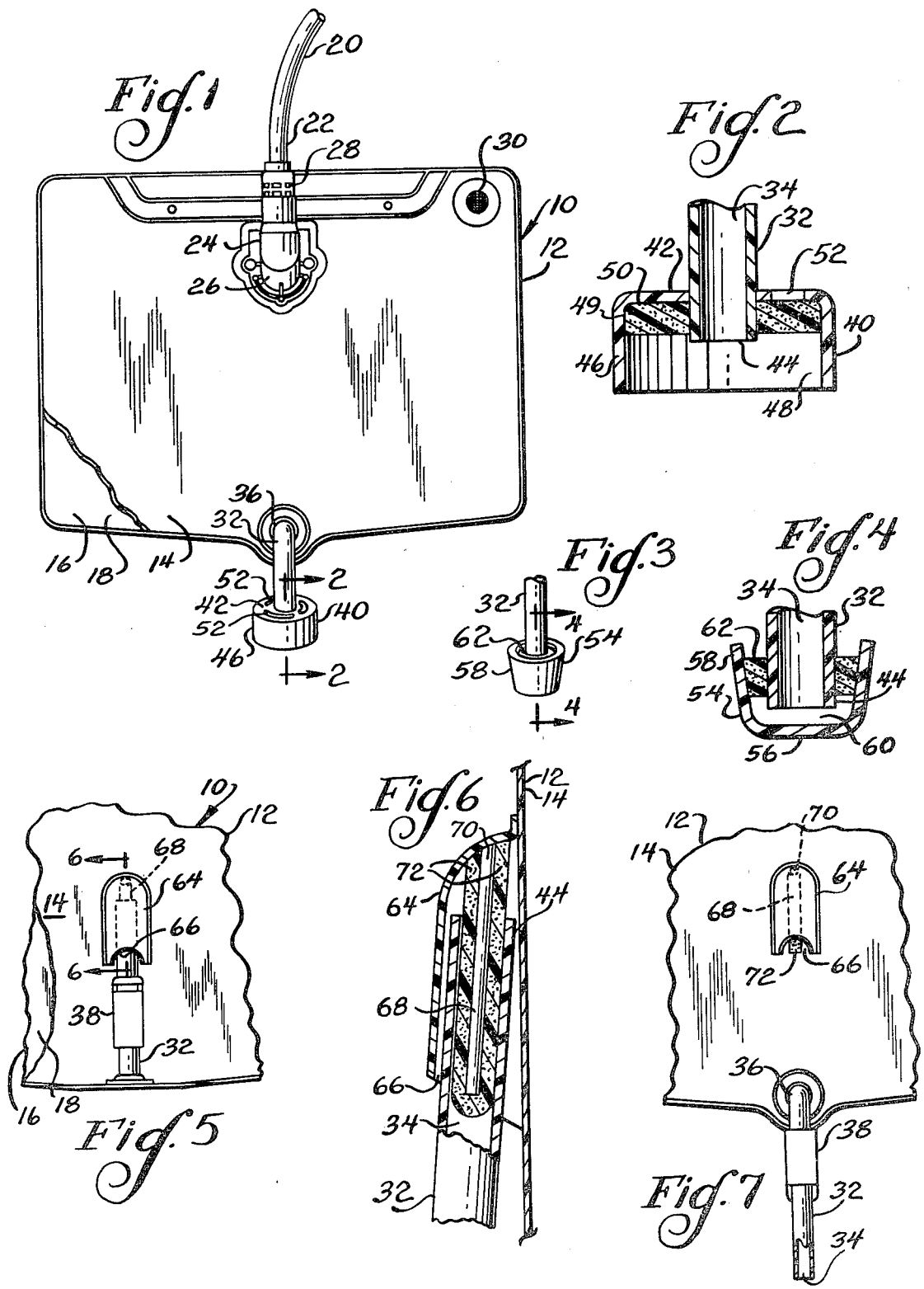

BODY DRAINAGE RECEPTACLE WITH ANTI-SEPTIC CATHETER CONTACT SURFACE IN RECEIVING POCKET

This is a division, of application Ser. No. 139,301 filed Apr. 11, 1980, now U.S. Pat. No. 4,333,480.

BACKGROUND OF THE INVENTION

The present invention relates to urine receptacles.

Before the present invention, receptacles have been utilized for collecting urine from a patient while catheterized. In one form, the receptacles comprise a container having a chamber for collection of urine, and a drainage tube communicating with the chamber, with an upstream end of the drainage tube being attachable to a proximal end of a catheter in the patient. The receptacle may have a tubular section having an inner end communicating with a lower portion of the chamber, with the tubular section being utilized to drain urine from the container chamber. However, it has been found that the outer end of the tubular section is a common source of contamination, particularly after urine has been drained through the tubular section, and the bacteria may pass by retrograde migration through the wetted tubular section into the chamber, thus posing a risk of contamination for the patient.

SUMMARY OF THE INVENTION

A principal feature of the present invention is the provision of an improved receptacle for receiving urine from a patient.

The receptacle of the present invention comprises, a container having a chamber for collection of urine, and a tubular section having an inner end attached to a lower portion of the container and communicating with the chamber, and an outer end. The receptacle has means for contacting a surface of the outer end of the tubular section.

A feature of the present invention is that the contacting means retains an antimicrobial agent.

Another feature of the invention is that the antimicrobial agent is activated by drops of urine when urine is drained through the tubular section.

Yet another feature of the invention is that the antimicrobial agent kills bacteria in the urine when wetted.

Still another feature of the invention is that the contacting means and retained microbial agent minimizes the possibility of contamination to the container contents through the tubular section.

A feature of the present invention is that the contacting means may comprise an open cell foam located in contact with the outer end of the tubular section.

Another feature of the invention is that the foam may be located in a hood extending around the outer end of the tubular section.

Yet another feature of the invention is that the foam may be retained on a cap which is placed on the outer end of the tubular section.

Still another feature of the invention is that the foam may be retained in a pocket of the container which receives the outer end of the tubular section in a storage position of the tubular section.

Further features will become more fully apparent in the following description of the embodiments of this invention and from the appended claims.

DESCRIPTION OF THE DRAWINGS

In the drawings:

FIG. 1 is a fragmentary elevational view of a urine receptacle of the present invention having a tubular section for draining urine from a container of the receptacle;

FIG. 2 is a fragmentary sectional view taken substantially as indicated along the line 2—2 of FIG. 1;

FIG. 3 is a fragmentary perspective view of a cap for the tubular section in another embodiment of the receptacle of the present invention;

FIG. 4 is a fragmentary sectional view taken substantially as indicated along the line 4—4 of FIG. 3;

FIG. 5 is a fragmentary elevational view of another embodiment of the urine receptacle showing an outer end of the tubular section being received in a pocket in a storage position of the tubular section;

FIG. 6 is a fragmentary sectional view taken substantially as indicated along the line 6—6 of FIG. 5; and FIG. 7 is a fragmentary elevational view showing the tubular section removed from the pocket in a drainage position of the tubular section.

DESCRIPTION OF THE PREFERRED EMBODIMENTS

Referring now to FIG. 1, there is shown a receptacle generally designated 10 having a container 12 with a front wall 14 and a back wall 16 of flexible plastic material, with the front and back walls 14 and 16 being joined around their periphery to define a chamber 18 between the front and back walls 14 and 16. The receptacle 10 has a drainage tube 20 having a downstream end 22 attached to the front wall 14 of the container 12 by a hollow connector 24 comprising a drip chamber 26 which may have suitable openings and a bacteria filter defining a vent 28 for the drip chamber 26. In use, an upstream end (not shown) of the drainage tube 20 is attached to a proximal end of a catheter (not shown) in the patient, such that urine drains through the catheter and drainage tube 20, and through the connector 24 into the chamber 18 of the container 12 for collection therein. The container 12 may have a suitable vent 30 on the front wall 14 with a bacteria filter of known type to filter bacteria passing from the atmosphere through the vent 30 into the chamber 18.

With reference to FIGS. 1 and 2, the receptacle 10 has an elongated hollow tubular section 32 of flexible plastic material having a lumen 34. The tubular section 32 has an inner end 36 attached to a lower portion of the container front wall 14, such that the lumen 34 of the tubular section 32 communicates with a lower portion of the container chamber 18. With reference to FIGS. 5 and 7, the tubular section 32 may have a clamp 38 of known type to releasably close the lumen 34 of the tubular section. Thus, when the clamp 38 is closed, the clamp 38 prevents passage of urine through the tubular section 32. Alternatively, the clamp 38 may be opened in order to permit passage of urine through the tubular section 32 in order to drain collected urine from the container chamber 18.

As shown in FIGS. 1 and 2, the receptacle 10 has a hood 40 having an inner wall 42 attached to an outer end 44 of the tubular section 32. The hood 40 has an annular sidewall 46 extending outwardly from the inner wall 42, with the inner wall 42 and sidewall 46 defining a cavity 48. The tubular section 32 extends through the inner wall 42 of the hood 40, with the outer end 44 of the tubular section 32 being located in the cavity 48 of the hood 40 and being spaced from an outer edge of the sidewall 46, such that the outer end 44 of the tubular section 32 and the sidewall 46 of the hood 40 define an annular groove 49 extending around the outer end 44 of the tubular section 32. The receptacle 10 has a ring 50 of porous material such as open-cell urethane foam, located in the groove 49 with the ring 50 contacting an outer surface of the outer end 44 of the tubular section 32. The ring 50 of foam material is soaked in an antimicrobial agent or antiseptic solution, such as chlorhexidene gluconate, povidone iodine, or benzlkoniun chloride, and the ring 50 is permitted to dry out such that the antimicrobial agent is deposited upon strands of the foam. In a preferred form, the inner wall 42 of the hood 40 has a plurality of openings 52 extending through the inner wall 42 and communicating with the groove 49.

In use, the hood 40 prevents contact of the outer end 44 of the tubular section 32 by the user's hands in order to reduce the possibility of contamination to the tubular section 32 by the hands. The openings 52 in the inner wall 42 permit passage of air to ventilate the groove 49 and reduce buildup of heat in order to minimize the possibility of contamination inside the hood 40. After drainage of urine through the tubular section 32, any droplets of urine remaining at the outer end 44 of the tubular section 32 which contact the ring 50 activate the dry antimicrobial agent in the ring 50 in order to kill bacteria in the droplets of urine. Thus, the ring 50 and antimicrobial agent minimizes the possibility of contamination in the hood 40, and the possibility of retrograde bacterial movement through the tubular section 32 into the container chamber, which would otherwise pose a risk of danger to the catherized patient.

Another embodiment of the present invention is illustrated in FIGS. 3 and 4, in which like reference numerals designate like parts. In this embodiment, the receptacle 10 has a cap 54 having a bottom wall 56 and a generally annular sidewall 58 extending from the bottom wall 56, such that the bottom wall 56 and sidewall 58 define a cavity 60 in the cap 54. As shown, the cap 54 has a ring 62 of porous material which is attached to the inner surface of the sidewall 58. The ring 62 may comprise the foam material impregnated with an antimicrobial agent, as previously discussed in connection with the receptacle of FIGS. 1 and 2.

In use, the cap 54 is placed on the outer end 44 of the tubular section 32 with the ring 62 contacting the outer surface of the tubular section outer end 44. When it is desired to drain urine through the tubular section 32, the cap 54 is removed from the tubular section 32, and urine drains through the tubular section in order to empty the container 12. After drainage has been completed, the cap 54 is again placed on the outer end 44 of the tubular section 32, with the ring 62 of foam material contacting the outer surface of the tubular section outer end 44. Thus, any droplets of urine which remain on the outer surface of the tubular section contact the antimicrobial agent in the ring 62 in order to activate the antimicrobial agent and kill the bacteria on the tubular section 32. In this manner, the cap 54 of FIGS. 3 and 4 minimizes the possibility of retrograde bacteria movement through the tubular section 32 into the container chamber 18.

Another embodiment of the present invention is illustrated in FIGS. 5-7, in which like reference numerals designate like parts. In this embodiment, the container 12 has an elongated pocket 64 defining an open end 66 to receive the outer end 44 of the tubular section 32 in a storage position of the tubular section 32. The receptacle 10 has an elongated projection 68 having an inner end 70 secured to an inner end of the pocket 64, with the projection extending toward the open end 66 of the pocket 64, such that the projection 68 is received in the outer end 44 of the tubular section 32 when the outer end 44 of the tubular section 32 is located in the pocket 64. As shown, the projection 68 has a strip 72 of porous material extending along opposed sides of the projection 68. The porous material of the strip 72 may comprise the open cell foam impregnated with the described antimicrobial agent, as discussed in connection with FIGS. 1 and 2 of the present invention.

In use, the outer end 44 of the tubular section 32 is inserted into the open end 66 of the pocket 64, such that the projection 68 and strip 72 are received in the lumen 34 of the tubular section 32. Thus, the projection 68 and strip 72 are located in the tubular section 32 in the storage position of the tubular section 32. When it is desired to drain urine from the container chamber, the outer end 44 of the tubular section 32 is removed from the pocket 64, such that the projection 68 and strip 72 are also removed from the lumen 34 of the tubular section 32, and the clamp 38 is opened in order to permit drainage of urine through the tubular section 32 in a drainage position of the tubular section 32, as shown in FIG. 7. After drainage of urine has been completed, the clamp 38 is again closed, and the outer end 44 of the tubular section 32 is again inserted into the open end 66 of the pocket 64, such that the projection 68 and strip 72 are received in the lumen 34 of the tubular section 32. Thus, the impregnated strip 72 of the projection 68 wipes the inner surface of the outer end 44 of the tubular section 32, such that any droplets of urine remaining after drainage of the container will activate the antimicrobial agent in the strip 72. In this manner, the antimicrobial agent kills bacteria in the tubular section, and minimizes the possibility of retrograde bacterial movement through the tubular section 32 into the container chamber 18.

In the described embodiments, it will be seen that the impregnated foam may contact either the inner or outer surface of the tubular section, and the impregnated foam retains the antimicrobial agent in a dry form to permit wetting of the antimicrobial agent by the urine in order to kill bacteria in the urine droplets.

The foregoing detailed description is given for clearness of understanding only, and no unnecessary limitations should be understood therefrom, as modifications will be obvious to those skilled in the art.

We claim:
1. A urine receptacle, comprising:
a container having a chamber for collection of urine, and a pocket on an outer surface of the container, said pocket having an open end;
a tubular section having an inner end attached to a lower portion of the container and communicating with said chamber, and an outer end; and
an elongated projection means extending from the container and secured in said pocket and being removably receivable in a lumen of the tubular section in said outer end in a storage position of the tubular section in said pocket, said projection means having means for contacting an inner surface of the tubular section and for retaining an antimicrobial agent.

2. The receptacle of claim 1 wherein the contacting and retaining means comprises a strip of porous material extending along opposed sides of said projection.

3. The receptacle of claim 2 wherein said strip comprises an open cell foam.

4. The receptacle of claim 1 wherein said container includes a pocket on the outer surface of the container, said pocket having an open end to receive the outer end of the tubular section in said storage position, said projection being located in said pocket and extending toward said open end of the pocket such that said projection is received in the tubular section when said outer end of the tubular section is received in the pocket.

5. A urine receptacle, comprising:
 a container having an outer surface and having a chamber for collection of urine and a pocket on the outer surface of the container, said pocket having an open end;
 a tubular section with a central lumen and having an inner end attached to a lower portion of the container and communicating with said chamber, and an outer end removably receivable in the open end of said pocket in a storage position of the tubular section; and
 means in said pocket for contacting the lumen of the outer end of the tubular section and for retaining an antimicrobial agent.

6. The receptacle of claim 5 wherein the contacting and retaining means comprises a porous material.

7. The receptacle of claim 5 wherein the contacting and retaining means comprises a foam material.

* * * * *